United States Patent [19]

White et al.

[11] Patent Number: 5,438,271
[45] Date of Patent: Aug. 1, 1995

[54] BIOSENSING METER WHICH DETECTS PROPER ELECTRODE ENGAGEMENT AND DISTINGUISHES SAMPLE AND CHECK STRIPS

[75] Inventors: Bradley E. White, Indianapolis; Robert A. Parks, Springport; Paul G. Ritchie, Indianapolis, all of Ind.

[73] Assignee: Boehringer Mannheim Corporation, Indianapolis, Ind.

[21] Appl. No.: 343,363

[22] Filed: Nov. 22, 1994

Related U.S. Application Data

[63] Continuation of Ser. No. 73,178, Jun. 8, 1993, abandoned.

[51] Int. Cl.⁶ .............................................. G01R 27/02
[52] U.S. Cl. ................................... 324/444; 324/525; 324/693; 204/406
[58] Field of Search ............... 324/438, 439, 446, 450, 324/603, 692, 693, 525, 538; 204/401, 406; 422/82.02

[56] References Cited

U.S. PATENT DOCUMENTS

| | | | |
|---|---|---|---|
| 3,992,598 | 11/1975 | Steuer et al. | 200/81.9 M |
| 3,996,514 | 12/1976 | Brown et al. | 324/722 |
| 4,123,701 | 10/1978 | Josefsen et al. | 324/448 |
| 4,178,543 | 12/1979 | Wrinn et al. | 324/421 |
| 4,680,537 | 7/1987 | Miller | 324/439 |
| 4,714,874 | 12/1987 | Morris et al. | 324/444 |
| 4,940,945 | 7/1990 | Littlejohn et al. | 324/438 |
| 4,999,582 | 3/1991 | Parks et al. | 324/438 |
| 5,053,199 | 10/1991 | Keiser et al. | 422/82.02 |
| 5,108,564 | 4/1992 | Szuminsky et al. | 204/153.12 |
| 5,266,179 | 11/1993 | Nankai et al. | 204/401 |

FOREIGN PATENT DOCUMENTS

0471986A2  2/1992  European Pat. Off. .

Primary Examiner—Kenneth A. Wieder
Assistant Examiner—Christopher M. Tobin
Attorney, Agent, or Firm—Perman & Green

[57] ABSTRACT

A biosensing meter receives a biomedical sample strip or a check strip, a sample strip including electrically isolated excitation and sense electrodes. The biosensing meter includes first and second contacts that are positioned to be electrically connected by a sense electrode when a sample strip is inserted into the biosensing meter. An operational amplifier circuit has one input connected to the first contact and a second input connected to a reference potential, the one input manifesting the reference potential as a result of a feedback within the operational amplifier. A processor is coupled to the second contact and determines the presence of the reference potential at the second contact when an inserted sense electrode connects the first and second contacts. The processor also distinguishes between a sample strip and a check strip and, when a sample strip is inserted, that the sample strip exhibits a proper impedance between its sense and excitation electrodes—to enable operation of the biosensing meter upon dosing of the sample strip.

10 Claims, 3 Drawing Sheets

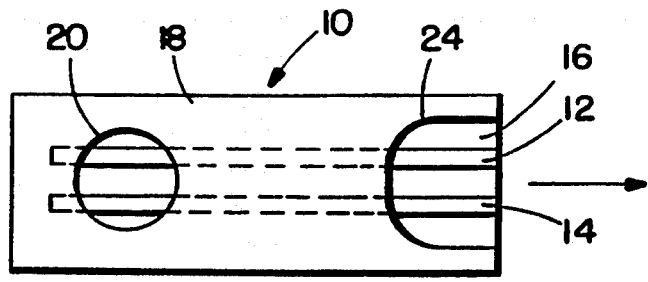
FIG. 1.
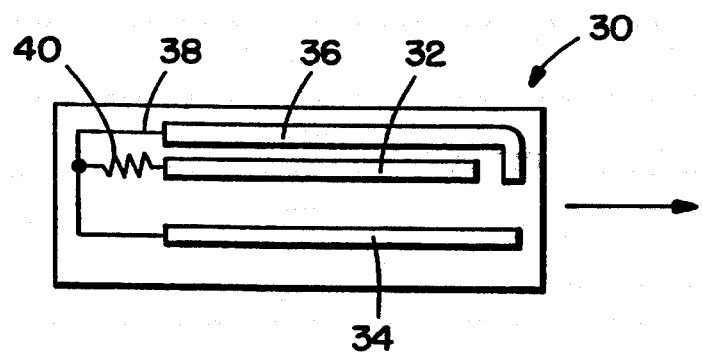
FIG. 2.
FIG. 3.
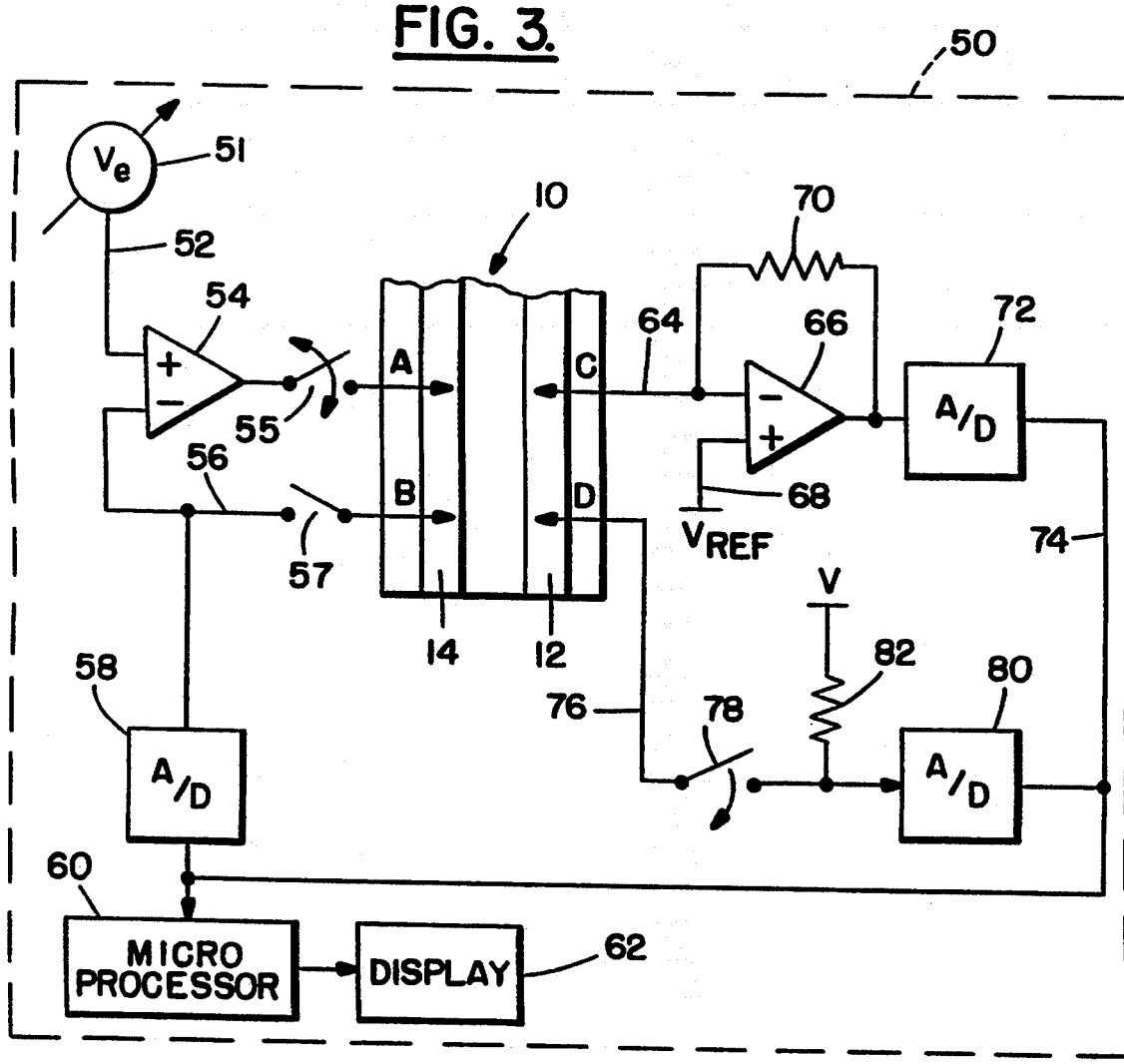

BIOSENSING METER WHICH DETECTS PROPER ELECTRODE ENGAGEMENT AND DISTINGUISHES SAMPLE AND CHECK STRIPS

This is a continuation of application Ser. No. 08/073,178 filed on Jun. 8, 1993, now abandoned.

FIELD OF THE INVENTION

This invention relates to biosensing instruments for detecting analyte concentrations and, more particularly, to such instruments that employ disposable sample strips.

BACKGROUND OF THE INVENTION

Biosensing instruments that employ disposable sample strips enjoy wide consumer acceptance. Such instruments are employed for the detection of analytes such as glucose and cholesterol levels in blood samples and, in general, provide accurate readings if the user is careful to follow the instrument's directions. More often than not, however, the user is careless in the use of either the sample strip or the instrument and erroneous readings result. Accordingly, significant efforts have been taken by instrument manufacturers to reduce the potential for errors during the use of sample strips and instruments.

Even if a biosensing instrument and sample strips are employed properly, the presence of a manufacturing defect in either will cause erroneous readings. Thus, while great care is taken in the production of such instruments and sample strips, there is a need to incorporate analytical procedures in the instrument that enable instrument malfunctions, sample strip irregularities, and user errors to be detected so as to prevent erroneous analyte readings.

The prior art includes a number of disclosures of biosensing instruments that employ disposable sample strips. In U.S. Pat. No. 5,108,564 to Szuminsky et al., a biosensing instrument is disclosed that measures glucose concentrations in blood. The instrument depends upon a reaction wherein glucose, in the presence of an enzyme, catalyzes a reaction of potassium ferricyanide to potassium ferrocyanide. After the reaction has completed, a voltage is applied across a reaction zone and causes a reversal of the reaction with an accompanying generation of a small, but measurable current. That current is termed the Cottrell current and, in dependence upon the concentration of glucose in the reaction zone, follows a predetermined curve during the reverse reaction. A reading of the Cottrell current is converted into an indication of glucose concentration. The instrument senses an impedance across the reaction zone and determines when a blood sample has been emplaced therein by detecting a sudden change in current flow. At such time, an incubation period is commenced, followed by application of a potential across the reaction zone and measurement of the Cottrell current.

European Patent Application 0 471 986 A2 of Tsutsumi et al. discloses a blood glucose measurement system that employs disposable sample strips. The Tsutsumi et al. system detects the presence of a blood sample by sensing a resistance across a pair of electrodes. It further employs a plurality of sensor-like strips, each having a specific resistance value which identifies it from other strips. Each of these strips has a particular application, i.e., for use during an adjustment mode of the instrument, during an error compensation mode, during a calibration mode, etc.

U.S. Pat. No. 4,999,582 to Parks et al., assigned to the same Assignee as this application, describes a biosensor electrode excitation circuit for determining if a sample strip has been properly inserted into a meter and if at least one electrode on the sample strip exhibits a proper level of contact resistance. U.S. Pat. No. 4,123,701 to Josefsen et al. also describes a dual electrode sample strip which employs a recessed well for receiving a biological sample. The instrument which receives the sample strip is provided with an opening that accommodates the sample strip and prevents its insertion in an erroneous manner. In U.S. Pat. No. 3,922,598 to Steuer et al., an electrical resistance system is described for measuring hematocrit of a blood sample. In this instance, however, an electrode probe is employed for measuring the required resistance value—rather than a disposable sample strip.

U.S. Pat. No. 4,940,945 to Littlejohn et al. describes an interface circuit for use in a biochemical sensing instrument. A disposable cartridge is employed that includes a pair of electrodes across which resistance measurements are taken. Circuitry is disclosed for sensing the presence of a fluid sample by an initial resistance measurement. In FIG. 10, Littlejohn et al. indicate that electrical contact is made to an electrode by a pair of measurement contacts so that a current flows that is sufficiently high to create a microweld—for purposes of improved electrical contact. U.S. Pat. No. 3,996,514 to Brown et al. employs plural electrodes to enable contact resistance to be measured and monitored during use of a circuit board.

Accordingly, it is an object of this invention to provide a biosensing meter with an ability to determine whether a sample strip has been properly or improperly inserted.

It is another object of this invention to provide a biosensing meter with the capability for discriminating between a sample strip and a check strip.

It is another object of this invention to provide a biosensing meter that accepts reusable sample strips and determines the quality of the sample strip upon its insertion.

SUMMARY OF THE INVENTION

A biosensing meter receives a biomedical sample strip or a check strip, a sample strip including electrically isolated excitation and sense electrodes. The biosensing meter includes first and second contacts that are positioned to be electrically connected by a sense electrode when a sample strip is inserted into the biosensing meter. An operational amplifier circuit has one input connected to the first contact and a second input connected to a reference potential, the one input manifesting the reference potential as a result of a feedback within the operational amplifier. A processor is coupled to the second contact and determines the presence of the reference potential at the second contact when an inserted sense electrode connects the first and second contacts. The processor also distinguishes between a sample strip and a check strip and, when a sample strip is inserted, that the sample strip exhibits a proper impedance between its sense and excitation electrodes—to enable operation of the biosensing meter upon dosing of the sample strip.

DESCRIPTION OF THE DRAWINGS

FIG. 1 is a plan view of a sample strip.

FIG. 2 is a plan view of a check strip with a top cover removed.

FIG. 3 is a circuit/block diagram of a biosensing meter that embodies the invention.

DETAILED DESCRIPTION OF THE INVENTION

Figure 4:
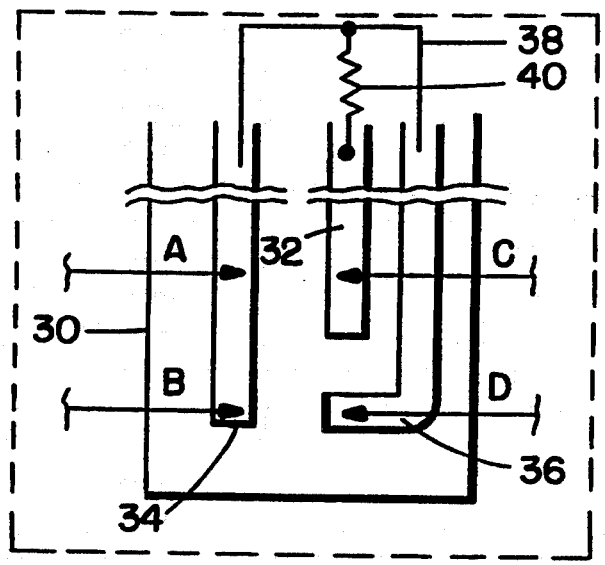
FIG. 4 shows a circuit arrangement when a check strip is inserted into the biosensing meter of FIG. 3.

Referring to FIG. 1, sample strip 10 comprises a pair of electrodes 12 and 14 which are supported on a polymeric support 16. A cover sheet 18 is provided with openings 20 and 24 which expose electrodes 12 and 14. Opening 20 creates a well and defines a reaction zone between electrodes 12 and 14. A layer (not shown) of enzymatic reactants overlays electrodes 12 and 14 and provides a substrate on which an analyte—containing fluid sample can be emplaced. Opening 24 exposes electrodes 12 and 14 so that when sample strip 10 is inserted into a biosensing meter, electrical connection can be made thereto.

In FIG. 2, a check strip 30 is shown that is employed to determine the operability of the biosensing meter and to enable an exercise of certain of its measurement functions. Check strip 30 includes a pair of electrodes 32 and 34 which correspond in placement to sense and excitation electrodes 12 and 14 (FIG. 1) respectively. Electrode 32 is foreshortened and is bounded by an L-shaped electrode 36 that is shorted by wire 38 to electrode 34. A resistance 40 connects electrodes 32 and 36 to electrode 32. As will be hereafter understood, check strip 30 enables an exercise of a biosensing meter's measurement functions.

In FIG. 3, a schematically illustrated biosensing meter 50 includes a window (not shown) for accepting either a sample strip 10 or a check strip 30. In FIG. 3, the distal portion of a sample strip 10 is shown in the inserted position. Excitation electrode 14, if it is continuous and properly inserted, electrically connects contacts A and B. Similarly, sense electrode 12 electrically shorts contacts C and D if sample strip 10 is properly inserted and a proper level of contact resistance is present. Contacts A, B and C, D are respectively spaced apart within biosensing meter 50 and enable a determination to be made that a sample strip 10 has been properly inserted and that its electrodes reflect the proper impedance states. Once such determinations are made, sample strip 10 may be dosed, i.e., a drop of analyte-containing fluid placed in opening 20.

As is shown in FIG. 4, when a check strip 30 is inserted into meter 50, electrode 34 makes electrical connections with contacts A and B, whereas electrode 32 connects to a contact C and electrode 36 connects to contact D.

Returning to FIG. 3, an excitation voltage $V_e$ is applied from variable source 51, via line 52, to operational amplifier 54. The output from operational amplifier 54 is connected via analog switch 55 to contact A. A second input to amplifier 54 is connected to contact B via line 56 and analog switch 57. The second input to amplifier 54 is also connected to analog to digital converter (A/D) 58. The output from A/D converter 58 is applied to a microprocessor 60 which is, in turn, provided with a display 62. Switches 55 and 57 are only opened during a time that the chemical reaction is occurring in well 20, so as to assure a high impedance condition thereacross. At other times, switches 55 and 57 are closed.

On the sense side of biosensing meter 50, a line 64 connects contact C to one input of operational amplifier 66. Another input of operational amplifier 66 is connected via line 68 to a reference potential. A resistor 70 provides the normal feedback function for operational amplifier 66. The output from operational amplifier 66 is applied via A/D converter 72 to bus 74 where it is applied as an input to microprocessor 60.

Contact D is connected via conductor 76 and a multiplex switch 78 to A/D converter 80, whose output is, in turn, connected to bus 74. A supply voltage source V is connected via resistor 82 to the input to A/D converter 80. Switch 78 is closed when meter 50 is initially powdered so as to enable a determination to be made of the proper insertion of sense electrode 12. Once that determination is made, switch 78 is opened.

Figure 5:
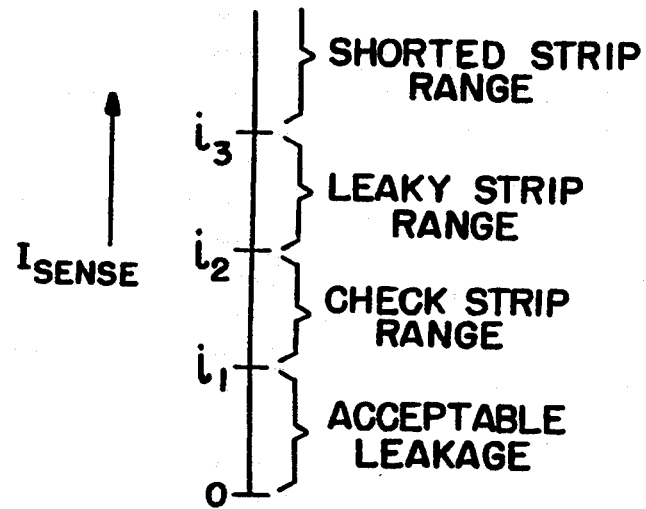
FIG. 5 is a diagram illustrating levels of sensed currents that enable strip type discriminations to be made and a determination of the quality of an inserted strip.

Prior to describing the operation of the circuit shown in FIG. 3, reference should be made to FIG. 5 wherein certain sensed current levels are shown. If a current is sensed flowing between electrodes 12 and 14 that falls between 0 and $i_1$, a determination is made that a sample strip 10 has been inserted and that the sensed current falls within an acceptable current leakage range. (Recall that a sample strip 10 is not dosed prior to insertion, but only after biosensing meter 50 has determined that a sample strip 10 is properly inserted and acceptable). If a current is sensed that falls between $i_1$ and $i_2$, biosensing meter 10 determines that a check strip 30 has been inserted and proceeds to perform additional instrument test operations. If the sensed current falls between $i_2$ and $i_3$, biosensing meter 50 determines that a test strip 10 has been inserted, but that it evidences an excessive leakage current which requires that the strip be rejected. Finally, if the sensed current exceeds $i_3$, it is determined that a short circuit exists and the meter is automatically shut down until the offending strip is removed.

Figure 6:
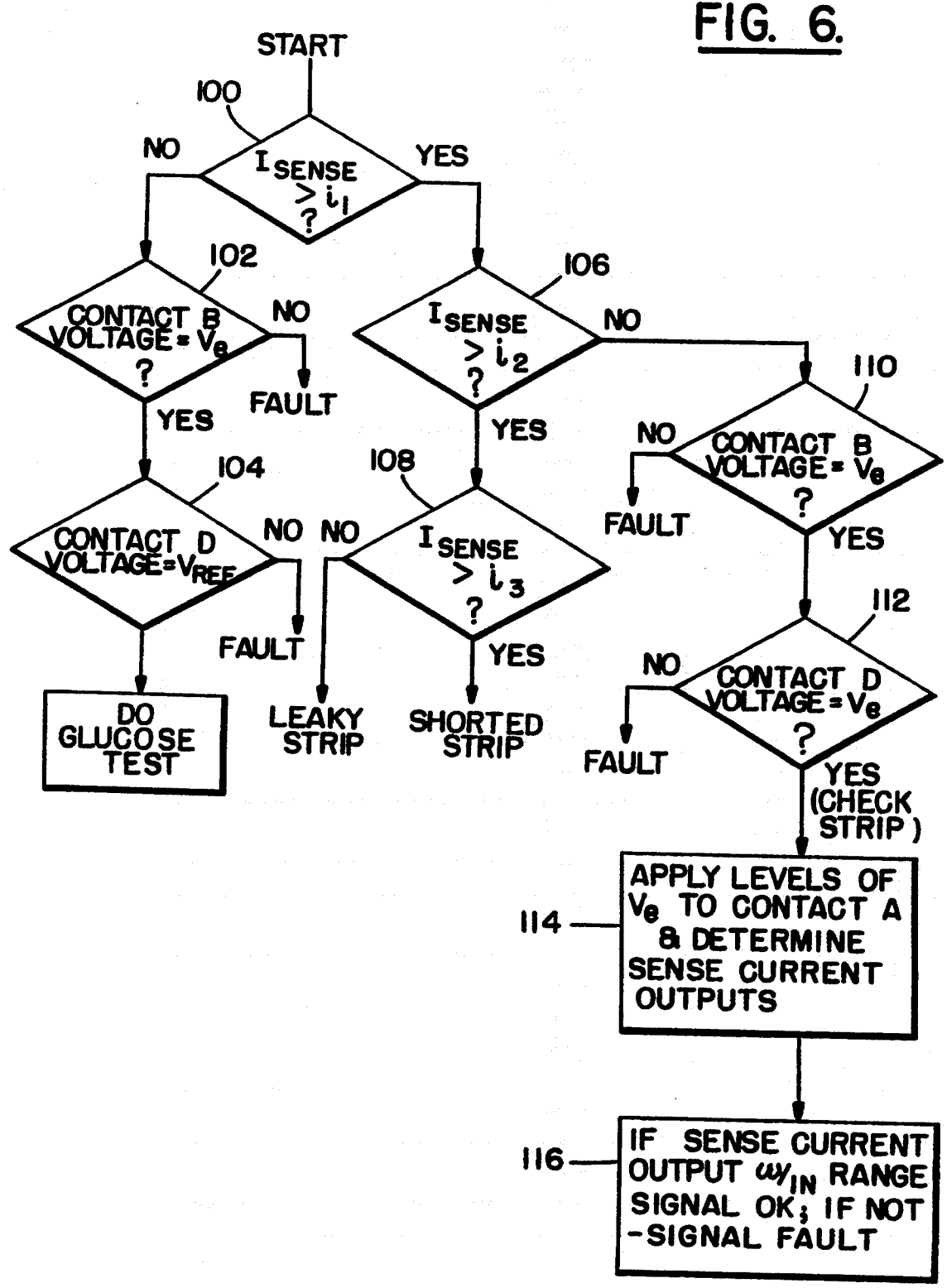
FIG. 6 is a flow diagram illustrating the operation of the circuit of FIG. 3.

The operation of the circuit shown in FIGS. 3 will now be described in conjunction with the logic flow diagram of FIG. 6. It is initially assumed that either a sample strip 10 or a check strip 30 has been inserted into meter 50. The insertion of a strip is determined by either an excitation electrode 14 shorting contacts A and B together or a sense electrode 12 shorting contacts C and D together. When contact A is shorted to contact B, an excitation voltage $V_e$ applied to contact A via operational amplifier 54 appears at the input to A/D converter 58. The resulting output from A/D converter 58 enables micro-processor 60 to detect the insertion of strip 12. In addition, micro-processor 60 continues to monitor that output from A/D converter 58 to verify the applied level of $V_e$ and that strip 10 is not removed prematurely.

In a similar manner, when a sense electrode 12 shorts contact C to contact D, the potential at contact D (Formerly at supply voltage $+V$) is clamped to reference potential 68 by the action of operational amplifier 66.

At the start of operation of the circuit of FIG. 3, it is assumed that meter 50 has been powered and that switch 78 is closed. In addition, an excitation potential $V_e$ is applied from source 51 via operational amplifier 54 to contact A. As shown in decision box 100 in FIG. 6, microprocessor 60 initially determines whether the current sensed at contact C exceeds $i_1$. If not, it is determined that the sensed current falls within an acceptable leakage range for a sample strip 10.

Further tests are now run to assure that sample strip 10 has been properly inserted into meter 50. The first test (decision box 102) determines whether a voltage is present on contact B that is equal to the applied excitation voltage $V_e$. If so, it is considered an indication that excitation electrode 14 is continuous and properly shorts contact A and B.

As above stated, A/D converter 58 senses the potential fed back from contact B via line 56. As the feedback from line 56 to operational amplifier 54 causes operational amplifier 54 to exhibit a unity gain characteristic, the voltage sensed on contact B ought to be equal to the excitation voltage $V_e$ from source 51. The voltage identity is determined by microprocessor 60 with a match in potentials indicating that the test has been passed. If the potentials do not match, a fault is indicated.

Next, the system determines whether the potential present on contact D reflects the reference potential applied via line 68 to operational amplifier 66. This will occur only if contact D is shorted to contact C and is clamped by operation of operational amplifier 66 to the reference potential level applied via line 68. If the potential on contact D is not equal to the reference potential, a fault is indicated. Assuming that the reference potential is sensed, the system proceeds to indicate to the user that the test strip should be dosed and that the glucose test should then proceed.

Referring back to decision box 100, if the sensed current is determined to exceed $i_1$, the procedure moves to decision box 106 where it is determined whether the sensed current exceeds $i_2$. If not, it is determined that the sensed current falls within a range designated as a check strip range. That current results from a flow of current to contact C through resistance 40 when excitation voltage $V_e$ is applied to contact A (see FIG. 4). As will be understood by those skilled in the art, the value of resistor 40 sets the current flow to contact C and assures that it will fall within the check strip range between $i_1$–$i_2$.

If the sensed current falls within the check strip range, the procedure moves to decision box 110 where the voltage at contact B is again tested in the same manner as described with respect to decision box 102. This tests that excitation electrodes 34 is properly shorting contact B to contact A. If the sensed potential at contact B is other than the excitation voltage, a fault is indicated.

If the excitation voltage $V_e$ is sensed at contact B, the procedure moves to decision box 112, where the voltage at contact D is tested to determine if it is equal to excitation voltage $V_e$ (contact D is shorted to contact A via line 38). If for some reason, electrode 32 is shorted to electrode 36 (see FIG. 4), then the potential at contact D will be clamped by operational amplifier 66 to the reference potential applied to its noninverting input. If, however, contact D is not shorted to contact C, the input to A/D converter 80 will be the excitation voltage value $V_e$. Thus, so long as A/D converter 80 senses $V_e$ at its input, that value causes microprocessor 60 to determine that a check strip 30 is present in meter 50.

Once the presence of a check strip is confirmed, the procedure causes an application of a plurality of excitation voltage levels to operational amplifier 54. Each applied excitation voltage level causes a different current level to be sensed by operational amplifier 66 whose output, is in turn, converted to an appropriate digital level by A/D converter 72. Microprocessor 60 responds to each output from A/D converter 72 by determining if the outputs are within predetermined limits and thus indicates proper operation of meter 50. If appropriate digital values are determined (within limits), meter 50 is indicated as being operational. If the sensed current levels vary from the acceptable limits, a lockout indication is displayed to the user which indicates that a meter malfunction has occurred (box 116).

Returning briefly to decision box 106, if the sensed current is found to exceed $i_2$ then, as shown in decision box 108, it is further determined whether the sensed current exceed $i_3$. If yes, a shorted strip indication is given. If no, a leaky strip indication is given.

It should be understood that the foregoing description is only illustrative of the invention. Various alternatives and modifications can be devised by those skilled in the art without departing from the invention. For instance, A/D converters 58, 72 and 80 could be replaced by a sample A/D converter and fed by a multiplexer. Accordingly, the present invention is intended to embrace all such alternatives, modifications and variances which fall within the scope of the appended claims.

What is claimed is:

1. A biosensing meter for receiving a sample strip that includes electrically isolated excitation and sense electrodes that are bridged by an analyte reactant, said biosensing meter comprising:

a first contact and a second contact positioned to be electrically connected by said sense electrode when said sample strip is inserted into said biosensing meter;

operational amplifier means having one input connected to said first contact, a second input connected to a reference potential, an output, and a resistor directly connecting said output to said one input, whereby said one input is enabled to manifest said reference potential; and processor means coupled to said second contact and responsive to a presence of said reference potential at said second contact as an indication that said sense electrode connects said first and second contacts.

2. The biosensing meter as recited in claim 1, said processor means further comprising:

means for applying a voltage to said second contact, said processor means sensing said voltage until said sense electrode connects said first and second contacts, at which time said operational amplifier means enables said second contact to manifest said reference potential.

3. The biosensing meter as recited in claim 2 further comprising:

third and fourth contacts positioned to be electrically connected by said excitation electrode when a said sample strip is inserted into said biosensing meter; and means for determining, upon an insertion of said sample strip, that said third and fourth contacts are electrically connected.

4. The biosensing meter as recited in claim 3, further comprising:

means coupling said output of said operational amplifier means to said processor means; and excitation supply means coupled to said third contact for applying an excitation voltage thereto, said processor means responding to an output from said operational amplifier that is at or below a first threshold level when said excitation voltage is applied to said third contact and to a connected excitation electrode, by determining that said sample strip exhibits a requisite level of electrical isolation between its excitation and sense electrodes.

5. The biosensing meter as recited in claim 4, wherein if said operational amplifier provides an output in excess of a second threshold level, said processor determines that said sample strip exhibits either too high a level of leakage current or an electrical short condition.

6. A biosensing meter for receiving said sample strip or a check strip, said sample strip including electrically isolated excitation and sense electrodes that are bridged by an analyte reactant, said biosensing meter including first and second contacts positioned to be electrically connected by said sense electrode when said sample strip is inserted into said biosensing meter, said check strip including an excitation electrode and a segmented sense electrode, a first sense electrode segment aligned with said first contact and a second sense electrode segment aligned with said second contact, both said sense electrode segments making respective electrical connections with said first and second contacts upon insertion of said check strip into said biosensing meter, said first sense electrode segment also connected via a first resistance to said check strip's excitation electrode, said biosensing meter further comprising:

operational amplifier means having one input connected to said first contact, a second input connected to a reference potential, and an output directly connected by a second resistance to said one input to create a feedback path, whereby said one input manifests said reference potential; and processor means coupled to said second contact and responsive to a presence of said reference potential at said second contact as an indication that a sample strip is present and has a sense electrode that electrically connects said first and second contacts.

7. The biosensing meter as recited in claim 6 further comprising:

means coupling said output of said operational amplifier means to said processor means; and excitation means for applying an excitation voltage to an inserted excitation electrode of said check strip, and for causing, via said first resistance, a voltage to appear at said sense electrode which exceeds a first threshold, said processor means responsive to an output from said operational amplifier means that a voltage is present on said sense electrode that exceeds said first threshold to determine that said check strip is present in said biosensing meter.

8. The biosensing meter as recited in claim 7 wherein said first resistance connecting said first sense electrode segment to said excitation electrode is instrumental in assuring that said check strip causes said operational amplifier output to exceed said first threshold.

9. The biosensing meter as recited in claim 8, wherein upon determining a presence of an inserted check strip, said processor means causes excitation means to apply a plurality of excitation voltages to said excitation electrode for testing operations of said biosensing meter.

10. A biosensing meter for receiving a sample strip that includes electrically isolated excitation and sense electrodes that are bridged by an analyte reactant, said biosensing meter comprising:

first and second contact positioned to be electrically connected by an excitation electrode when said sample strip is inserted into said biosensing meter;

excitation voltage means for producing an excitation voltage;

amplifier means having one input connected to said excitation voltage means a second differential input connected to said second contact and an output connected to said first contact;

switch means connected between said first contact and said amplifier output and between said second contact and said second input, said switch means closed at all times except when a chemical incubation reaction is occuring with said analyte reactant, at which time said switch means is open;

processor means coupled to said second contact for determining a presence of an excitation voltage at said second contact as an indication that said sample strip has been inserted and for monitoring said excitation voltage at said second contact at least when said switch means are closed, as an assurance of a continued presence of said sample strip, until a test is completed, and of application of a proper level of excitation voltage during a test.

* * * * *